(12) United States Patent
McKenna et al.

(10) Patent No.: US 7,934,424 B2
(45) Date of Patent: May 3, 2011

(54) ULTRASONIC MATERIAL MONITOR FOR DETERMINING A CHARACTERISTIC OF THE MATERIAL

(75) Inventors: Mark J. McKenna, White River Junction, VT (US); Joseph S. Heyman, Williamsburg, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 542 days.

(21) Appl. No.: 11/782,229

(22) Filed: Jul. 24, 2007

(65) Prior Publication Data

US 2008/0022773 A1 Jan. 31, 2008

Related U.S. Application Data

(60) Provisional application No. 60/832,952, filed on Jul. 25, 2006.

(51) Int. Cl.
 *G01N 29/07* (2006.01)
(52) U.S. Cl. .......................................... 73/602
(58) Field of Classification Search ............ 73/597, 73/598, 599, 600, 602
See application file for complete search history.

(56) References Cited

U.S. PATENT DOCUMENTS

| | | | |
|---|---|---|---|
| 3,679,985 A | 7/1972 | Fang et al. | |
| 4,062,227 A | 12/1977 | Heyman | 73/630 |
| 4,179,786 A | 12/1979 | Eshghy | |
| 4,363,242 A | 12/1982 | Heyman | 73/761 |
| 4,624,142 A | 11/1986 | Heyman | 73/597 |
| 5,154,081 A | 10/1992 | Thompson et al. | |
| 6,422,093 B2 | 7/2002 | Feller | |
| 6,632,177 B1 | 10/2003 | Phillips et al. | |
| 7,017,422 B2 | 3/2006 | Heyman et al. | |
| 7,052,854 B2 | 5/2006 | Melker et al. | |
| 2004/0177693 A1 | 9/2004 | Tenoudji et al. | |
| 2004/0182160 A9 | 9/2004 | Madaras et al. | |
| 2005/0072236 A1 | 4/2005 | Heyman et al. | |
| 2006/0119402 A1 | 6/2006 | Thomsen et al. | |

OTHER PUBLICATIONS

Written Opinion of the International Searching Authority mailed Jun. 5, 2008 in corresponding PCT Application No. PCT/US2007/016625.
Hikata et al., *Tunneling of Dislocation Kinks and the Effect of Dissipation*, Physical Review Letters, vol. 54, No. 22, Jun. 3, 1985, pp. 2418-2421. Cordié et al., *Acoustic-Power Dependence of the Sound Velocity in Amorphous PdSi at Very Low Temperatures: Transverse Relaxation Time*, Physical Review Letter, vol. 47, No. 2, Jul. 13, 1981, pp. 106-109.
Hikata et al., *Interaction of Dislocations with Electrons and with Phonons*, Physical Review Letters, vol. 24, No. 5, Feb. 2, 1970, pp. 215-218.

*Primary Examiner* — Daniel S Larkin
*Assistant Examiner* — Rose M Miller
(74) *Attorney, Agent, or Firm* — Nixon & Vanderhye P.C.

(57) ABSTRACT

A material characteristic measurement approach measures an internal state of a material by measuring the nonlinear shift in velocity induced by different acoustic energies. The technology for implementing this measurement approach is relatively simple, robust, permits portable measurements, does not require that an unloaded initial condition of the material be measured or otherwise known in order to determine a characteristic of the material, can be applied using one or more transducers, and does not require physical contact with the material. Some example material characteristics include a residual stress existing without any external mechanical force applied, applied stress, a fatigue state, age, an interference-fit fastener stress, bio-activity, a nanostructure mixture of the material, a heat treatment of the material, a cross-linking of polymers in the material, a bio-growth organization of the material, a clotting factor of blood or blood-like material, a cure of an adhesive or sealant material, or the microstructure of the material.

19 Claims, 9 Drawing Sheets

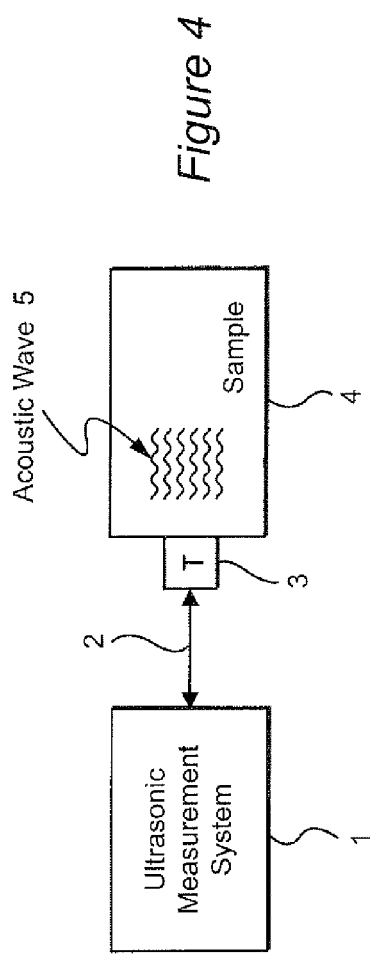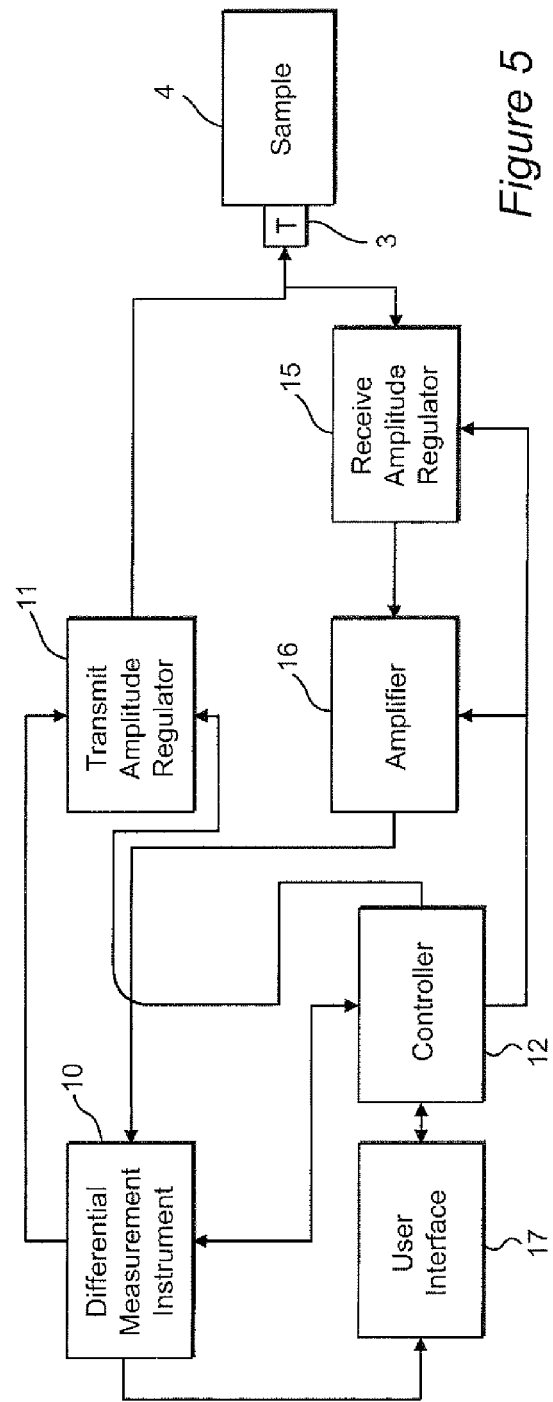

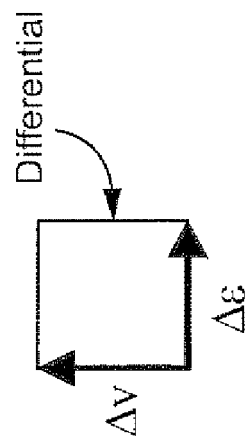
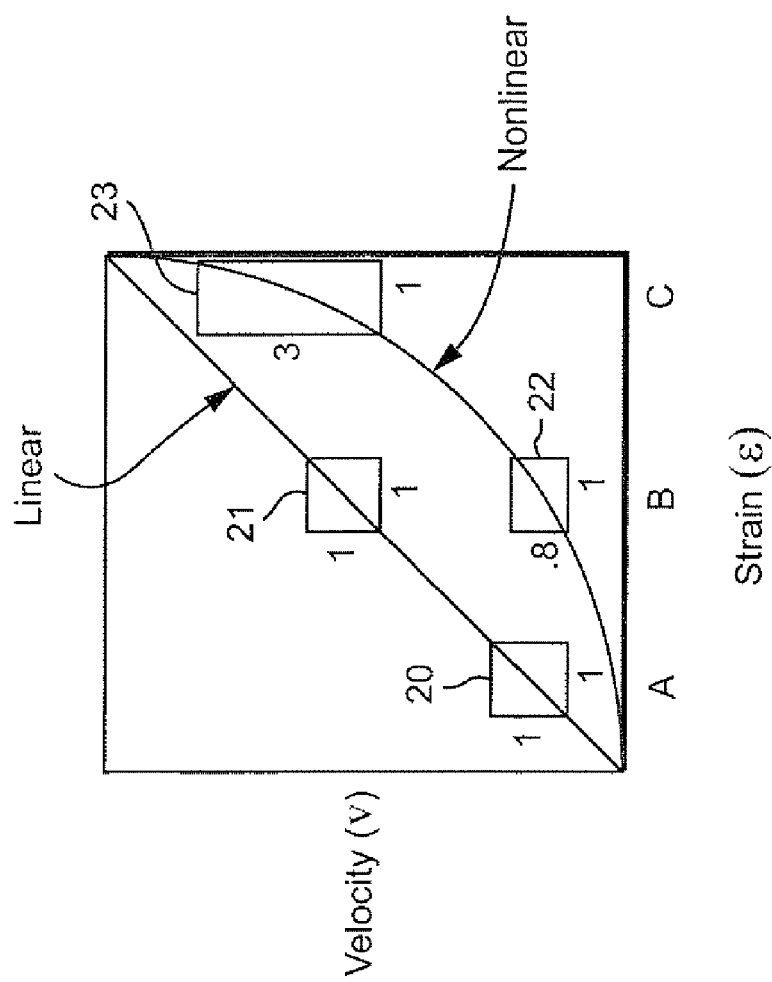
*Figure 6B*
*Figure 6A*

ULTRASONIC MATERIAL MONITOR FOR DETERMINING A CHARACTERISTIC OF THE MATERIAL

RELATED APPLICATION

This application claims the priority and benefit of U.S. Provisional patent application 60/832,952, filed Jul. 25, 2006, which is incorporated herein by reference in its entirety.

STATEMENT REGARDING FEDERALLY SPONSORED RESEARCH OR DEVELOPMENT

Work relating to this application was performed under US Navy Contract: N68335-06-C-0058.

TECHNICAL FIELD

The technical field relates to ultrasonic determination of material characterization and in particular stress which finds useful application in nondestructive material evaluation and quality control.

BACKGROUND

There are many applications in which the existing characterization or stress on a material or a portion of that material needs to be measured accurately and reliably. When stressed, the inter-atomic spacing of the lattice atoms of the material is displaced. Other conditions can alter the microstructure of the material as well, such as heat treatment or fatigue, for example. Past approaches to measure the stress state existing within a material have used very complex and expensive equipment that is difficult or impossible to move to a field site.

One stress measurement approach uses radiation. For example, an x-ray scattering measurement technique, called Laue Backscatter Diffraction, determines a change in lattice spacing based on the statistical scattering properties of the material. But Laue Backscatter Diffraction requires a radiation wavelength equal to the atomic spacing and specific angles to correspond exactly to the spacing of the atoms to create a sharp image of the coherence of the lattice. A similar technique utilizes a beam of Low Energy Electron Diffraction (LEED) images to acquire the same type of data. For electrons of energy ~20 eV (electron volts), the wavelength is about the same as for x-ray photons of ~20 keV (thousand electron volts) or about 2.5 Angstroms. Other stress measurement techniques based on radiation include neutron and synchrotron radiation. All radiation approaches are complex, require laboratory set-ups such as vacuum systems, radiation approval, complex shielding, and are very expensive and difficult to move out of the lab. Data interpretation is also complex and localized. Moving the measurement location also often produces different results.

Other stress measurement approaches are destructive, e.g., material is removed from the structure by drilling a hole. Destroying part of the material may create a significant flaw site and is generally not desired in critical structures. One destructive method mounts a strain gauge on the measurement site. At the center of the gauge, a small hole is drilled that relaxes the stress at and around the hole site. The strain gauge measures the small deformations in the remaining material that surround the hole. Another approach uses laser holography to examine the deformation at the site around the hole. Destructive mechanical microanalysis of a structure or a part is often used to examine grain micro-structure and alloy complexity with optical, electron, and x-ray analysis tools. These tools are all destructive in nature and can provide satisfactory assessment of a part undergoing destructive testing, but not of the actual part or material in its working environment.

Ultrasonic stress measurement approaches are based on changes in the ultrasonic propagation velocity with stress and microstructure. Early work on the measurement of bolt tension was based on the pulse-echo time-of-flight changes that occur when a fastener is placed under load. But these measurements require that the unloaded initial conditions of the bolt be measured before the bolt is stressed. As the bolt is loaded, it elongates and the velocity of sound propagating through the bolt changes. Both of these effects contribute to the altered time measured by the ultrasonic instrument. See for example U.S. Pat. No. 4,062,227.

Another stress measurement approach is based on a phase shift locking instrument called a pulsed phase locked loop as described for example in U.S. Pat. Nos. 4,363,242 and 4,624,142. The change in the frequency of the signal source locked to a specific phase point in a bolt or other object is determined. (A change in frequency is related to a change in velocity and length of the acoustic propagation). As the bolt elongates, the frequency drops keeping the phase of the system locked at a relative phase difference of ninety degrees (referred to as "quadrature"). Although the pulsed phase locked loop approach has a higher resolution than that achieved using the technique described in U.S. Pat. No. 4,062,227, it still requires an initial measurement of the unloaded material. Other ultrasonic approaches use combinations of compression, shear, and special polarization waves to determine changing stress states in a material. But they are more complex, requiring measurements along different paths, orientations, and/or polarizations.

For ferromagnetic materials, one can measure the changes in ultrasonic propagation during magnetic saturation. This approach, developed by Namkung and Heyman and described in "Residual Stress Characterization with an Ultrasonic/Magnetic Technique," Nondestructive Testing Communications, Vol. 5, September 1984, shows that the existing state of stress can be determined from the velocity change derivatives with respect to external magnetization. Barkhausen Noise is another derivative approach based on listening to the acoustic emissions that occur when ferromagnetic materials are magnetized. Depending on the initial state of stress, the emitted noise is altered during magnetization and gives some indication of the initial state of stress. This approach has been difficult to use quantitatively.

All of these ultrasonic stress and microstructure measurements are compromised by changes in thermal conditions because the speed of sound is strongly influenced by temperature. Therefore, the temperature of the material being analyzed must be determined, and if the temperature of the material is not uniform, the measurement is further complicated.

Given the various shortcomings and/or complexities of the stress and microstructure measurement approaches described above, a stress and microstructure measurement device is needed that is relatively simple, inexpensive, robust, preferably portable, and does not require that an unloaded initial conditions of the material be measured or otherwise known in order to determine a characteristic of the material like stress.

SUMMARY

A material characteristic measurement approach measures an internal state of a material by measuring the nonlinear shift in velocity induced by different acoustic energies. The technology described here for implementing this measurement approach is relatively simple, robust, permits portable measurements, does not require that an unloaded initial condition of the material be measured or otherwise known in order to determine a characteristic of the material, can be applied using one or more transducers, and does not require physical contact with the material. Some example material characteristics include: a residual stress existing in the material without any external mechanical force applied to the material, applied stress (such as a bridge member), a fatigue state associated with the material, the age of the material, an interference-fit fastener stress in a material, a bio-activity of a material, a nanostructure mixture of the material, a heat treatment of the material, a cross-linking of polymers in the material, a biogrowth organization of the material such as in a culture dish or film, a clotting factor of blood or blood-like material, a cure of an adhesive or sealant material, or the microstructure of the material.

An acoustic measurement of velocity or time-of-flight is made. An incremental amount of energy is acoustically added to the material. A change in the measurement is resolved. A non-linear parameter for the material is determined as a result of the acoustically added incremental energy. A characteristic of the material is then determined using the determined non-linear parameter such as those examples listed above.

The non-linear parameter may be associated with a derivative for the material resulting from the added incremental energy. In one non-limiting example embodiment relating to a material stress measurement application, the derivative is a strain derivative which may be determined in accordance with the following. A first acoustic signal having a first amplitude is applied to the material, and a first velocity of the first acoustic signal propagating through the material is determined. A second acoustic signal having a second amplitude different than the first amplitude is applied to the material, and a second velocity of the second acoustic signal propagating through the material is determined. A difference between the first and second velocities is divided by a difference between the first and second amplitudes to generate the strain derivative associated with the material.

In practice, these steps are repeated multiple times using different acoustic signal amplitudes or powers. One non-limiting implementation example uses a lookup table relating the nonlinear slope parameter for a material to a characteristic of that material. For the strain derivative example, a lookup table maps different strain derivatives to corresponding stress or strain values for the material. In that case, a stress or strain value for the material corresponding to the determined strain derivative can readily be retrieved from the lookup table. Different lookup tables may be generated for different types of materials and material treatments.

Because the relationship between different derivatives and the corresponding characteristic values for the material is nonlinear, a differential measurement instrument is preferably used. The resolution of the differential measurement instrument depends on the type of material being measured. In one example, the differential measurement instrument uses a phase comparison method (which can be implemented using analog or digital instrumentation) for determining the derivative.

In another non-limiting example embodiment, the difference between the first and second acoustic signal velocities related to a difference between the first and second acoustic signal amplitudes is used to generate an amplitude dependent slope parameter associated with the material, and a stress or other characteristic of the material is determined based on the amplitude dependent slope parameter. One non-limiting implementation example measures the first acoustic signal velocity indirectly by measuring a first time period for the first acoustic signal to propagate through the material and the second acoustic signal velocity indirectly by measuring a second time period for the second acoustic signal to propagate through the material. A first delay time is determined for a first acoustic signal having a first power level to propagate through the material, and a second delay time is determined for a first acoustic signal having a second power level to propagate through the material. A difference between the first and second delay times is related to a difference between the first and second power level to generate a non-linear parameter associated with the material at the second power level. The strain derivative is one example of a nonlinear slope parameter from which a material characteristic, in this case stress or strain, may be determined. A stress of the material is determined based on the non-linear parameter. Advantageously, the stress of the material is determined without knowledge of an initial stress condition of the material, its precise unstressed thickness, or without having to apply a mechanical force to the material.

It is not necessary that the change in velocity of the acoustic measurement wave be induced by a change in power of the acoustic measurement wave. For example, separate from the applied acoustic measurement wave, a first acoustic pumping wave may be applied to the material at a first power level followed by a second acoustic pumping wave applied to the material at a second, different power level. The change in power level in the material resulting from the first and second acoustic pumping waves causes a change in a velocity of the acoustic measurement wave propagating through the material. The change in velocity relative to the change in power level may then be used to determine the characteristic of the material, e.g., residual stress or strain, fatigue, age, interference-fit stress, microstructure, etc.

BRIEF DESCRIPTION OF THE DRAWINGS

FIG. 4 is a function block diagram for a material characteristic measurement system;

FIG. 5 is a function block diagram showing one non-limiting example of a material characteristic measurement device;

FIGS. 6A and 6B are graphs illustrating a linear and a non-linear relationship between acoustic velocity of a wave propagating through a material and a strain in the material;

DETAILED DESCRIPTION

The following description sets forth specific details, such as particular embodiments, procedures, techniques, etc. for purposes of explanation and not limitation. But it will be appreciated by one skilled in the art that other embodiments may be employed apart from these specific details. For example, non-limiting embodiments described below for purposes of illustration are directed to determining stress or strain in a material. But the technology described here may be used to determine a variety of characteristics of a material, examples of which include but are not limited to fatigue, age, strength, microstructure, interference-fit stress in a fastener, energy content, stiffness, bolt tension, torque in a shaft, heat treatment, plasticity, cold-work, nanostructure variations in mixtures, compressibility, or bioactivity of a material.

In some instances, detailed descriptions of well known methods, interfaces, circuits, and device are omitted so as not obscure the description with unnecessary detail. Moreover, individual blocks are shown in some of the figures. Those skilled in the art will appreciate that the functions of those blocks may be implemented using individual hardware circuits, using software programs and data, in conjunction with a suitably programmed digital microprocessor or general purpose computer, using application specific integrated circuitry (ASIC), and/or using one or more digital signal processors (DSPs).

Figure 1:
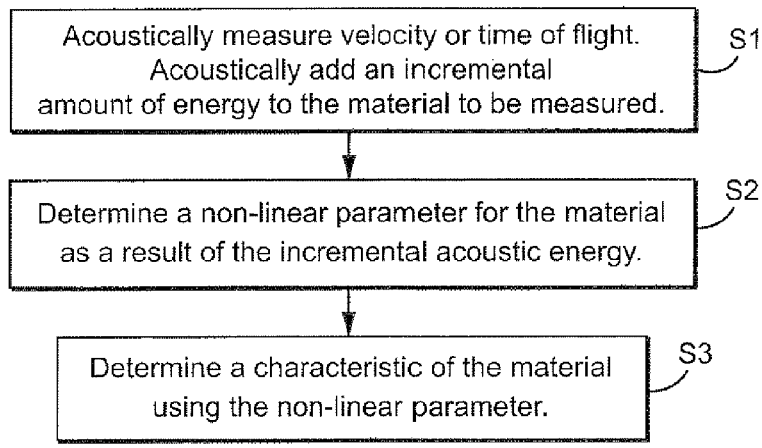
FIG. 1 is a flowchart diagram illustrating a non-limiting, example procedure for acoustically determining a characteristic of a material.

FIG. 1 is a flowchart diagram illustrating a non-limiting, example procedure for acoustically determining a characteristic of a material. An acoustic measurement of velocity or time-of-flight is made. An incremental amount of energy is acoustically added to the material (step S1). A non-linear parameter for the material is determined as a result of the acoustically added incremental energy (step S2). The characteristic of the material is then determined using the determined non-linear parameter (step S3). As mentioned above, non-limiting example material characteristics include one or more of the following: a residual stress existing in the material without any external mechanical force applied to the material, applied stress (such as a bridge member), a fatigue state associated with the material, the age of the material, an interference-fit fastener stress in a material, a bio-activity of a material, a nanostructure mixture of the material, a heat treatment of the material, a cross-linking of polymers in the material, a bio-growth organization of the material such as in a culture dish or film, a clotting factor of blood or blood-like material, a cure of an adhesive or sealant material, or the microstructure of the material.

Figure 2:
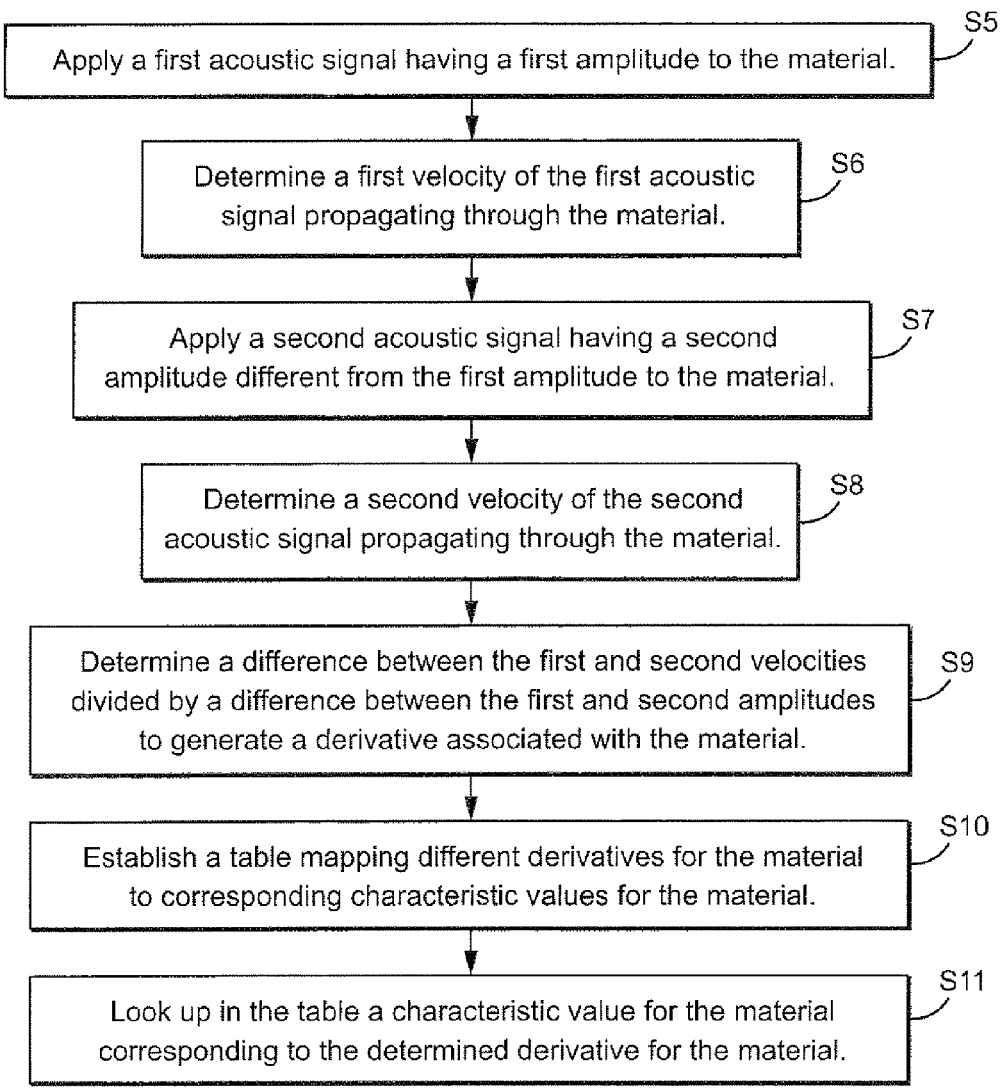
FIG. 2 is a flowchart diagram illustrating procedures for one non-limiting example way to acoustically determine a characteristic of a material.

FIG. 2 is a flowchart diagram illustrating procedures for one non-limiting example way to acoustically determine a characteristic of a material. The non-linear parameter in FIG. 1 may be associated with an acoustic signal velocity derivative with respect to power or amplitude for the material resulting from the added incremental energy. In a non-limiting example embodiment in which the characteristic of the material to be determined is a residual stress or strain, the acoustic signal velocity derivative is a strain derivative which may be determined in accordance with the steps described below. Stress and strain are different. Stress is the applied force, and strain is the affect of that force. There may be stress without strain and strain without stress. Other example velocity derivatives include pressure, temperature, magnetic field, electric field, etc. A first acoustic signal having a first amplitude to the material is applied (step S5). A first velocity of the first acoustic signal propagating through the material is then determined (step S6). A second acoustic signal having a second amplitude different than the first amplitude is applied to the material (step S7). A second velocity of the second acoustic signal propagating through the material is determined (step S8). A difference between the first and second velocities is divided by a difference between the first and second amplitudes to generate the derivative associated with the material (step S9). From the determined velocity/strain derivative, the characteristic of the material, e.g., residual stress, is determined. Alternatively, a power derivative could be used in which the change in power is divided by the change in velocity.

In practical applications, the method may be repeated multiple times using different acoustic amplitude or power levels. One non-limiting implementation example uses a lookup table. For the above example, such a table maps different velocity derivatives for the material to corresponding characteristic values for the material (step S10). In that case, a characteristic value for the material corresponding to the determined strain derivative for the material can readily be retrieved from the lookup table. Different lookup tables may be generated for different types of materials (step S11).

Figure 3:
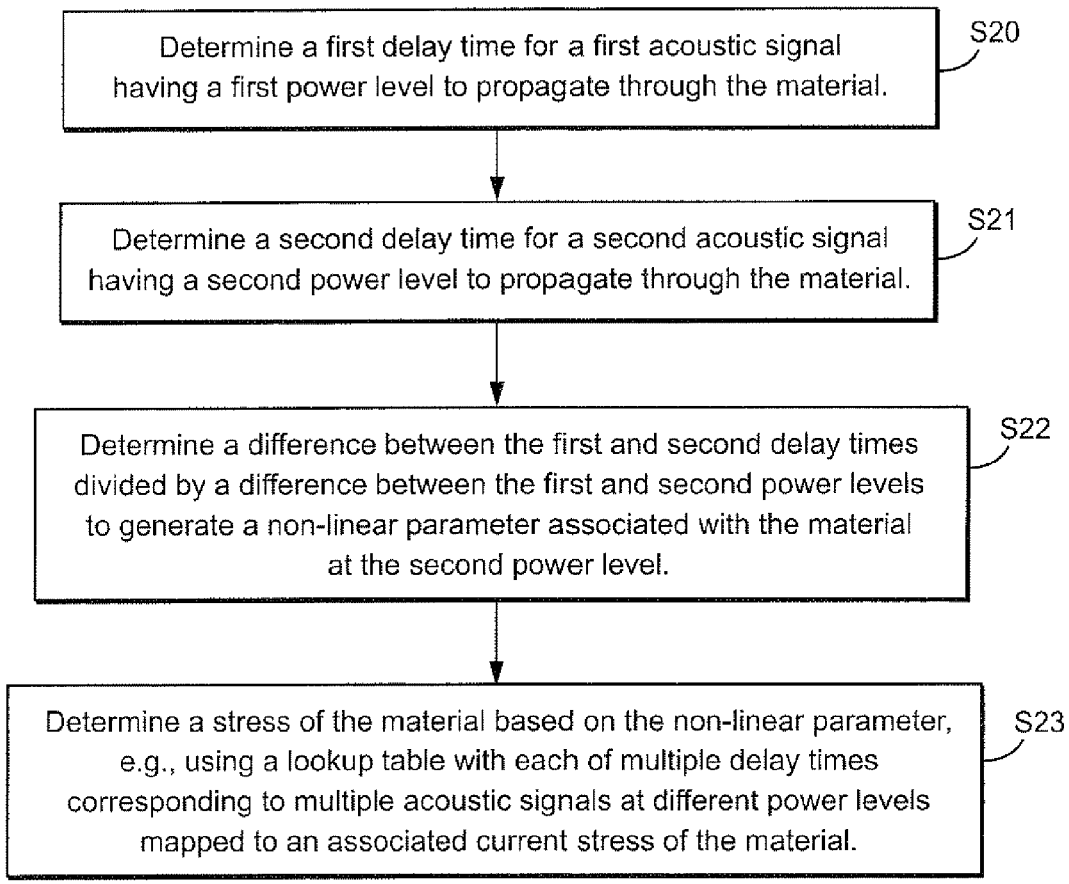
FIG. 3 is a flowchart diagram illustrating procedures for another non-limiting example way to acoustically determine a characteristic of a material.

FIG. 3 is a flowchart diagram illustrating procedures for another non-limiting example way to acoustically determine a characteristic of a material. A first delay time is determined for a first acoustic signal having a first power level to propagate through the material (step S20). A second delay time is determined for a first acoustic signal having a second power level to propagate through the material (step S21). A difference between the first and second delay times is divided by a difference between the first and second power level to generate a non-linear parameter associated with the material at the second power level (step S22). A stress of the material is determined based on the non-linear parameter (step S23). As above, a lookup table may be used to map residual stress of the material to a corresponding delay time and power level difference.

A non-limiting example of a material characteristic measurement system is shown in FIG. 4. Again, although the illustrative example relates to stress measurement, many different types of material characteristics may be determined using such a system. An ultrasonic measurement instrument 1 is connected via a connector 2 to an ultrasonic transducer (T) 3 that is acoustically coupled to a sample material 4 whose stress is to be measured. The ultrasonic measurement instrument 1 generates an electrical signal conveyed via connector 2 to excite the ultrasonic transducer 3. Non-limiting examples of an ultrasonic transducer include using piezoelectric ceramics such as lead zirconate titanate (PZT), lead metaniobate, single crystal disks such as Quartz or lithium niobate, EMAT devices for applications to conductors, and capacitive plates using electric fields. The ultrasonic transducer 3 converts the electrical signal into a mechanical wave and launches an acoustic wave 5 into the sample 4. The acoustic wave propagates through the sample and is reflected back to the transducer 3 which detects and converts the reflected acoustic wave into an electrical signal and returns that electrical. signal to the stress measurement instrument 1 via the connector 2.

FIG. 5 is a function block diagram showing one non-limiting example of a material characteristic measurement device. In this example and those that follow, a differential measurement instrument 10 is used to measure changes in velocity of the acoustic wave propagating through the material. Non-limiting examples of an ultrasonic differential measurement instrument based on acoustic signal phase changes include an analog pulsed phase locked loop based measurement system as described in U.S. Pat. Nos. 4,363,242 and 4,624,142 or a digital pulsed phase locked loop based measurement system as described in U.S. patent application to Lynch et. al. Ser. No. 11/806,475, filed on May 31, 2007, the contents of which are incorporated herein by reference. The digital pulsed phase locked loop based measurement system is particularly advantageous because of its high resolution capabilities. Other types of acoustic velocity measurement instruments having sufficient resolution to detect changes in acoustic velocity in the material being tested may be used.

The ultrasonic differential measurement instrument 10 provides an electrical pulse at a particular phase to a variable transmit amplitude regulator 11 controlled by a controller 12 to regulate the amplitude of the acoustic signal, e.g., a pulse, provided to the transducer 3. The acoustic output of the transmit amplitude regulator 11 drives the transducer 3 to propagate an acoustic wave towards the material sample 4 at the specified amplitude and phase. The transducer 3 receives a reflected acoustic pulse wave that propagated through the sample 4 and provides a corresponding electrical signal to a receive amplitude regulator 15 connected to an amplifier 16. The receive amplitude regulator 15 is connected back to the ultrasonic phase measurement instrument 10 thereby completing a phase locked loop. The controller 12 also controls the receive amplitude regulator 15, amplifier 16, the ultrasonic phase measurement instrument 10, and a user interface 17 that receives data from the ultrasonic phase measurement instrument 10 in synchronization with the controller 12. The ultrasonic phase measurement instrument 10 provides to the user interface 17 either the actual stress (or other characteristic) of the material sample or data from which that stress (or other characteristic) may be determined. The user interface 17 may store, display, process and/or transmit that data in any desired format.

The two amplitude regulators 11 and 15 are inverse regulators in the sense that as one increases amplitude, the controller 12 decreases amplitude of the other amplitude regulator by the same amount so that the phase locked loop amplitude is unchanged. This keeps the received signal constant at the phase locked loop based measurement instrument while the acoustic amplitude in the material sample 4 increases and decreases to acquire a derivative or slope parameter related to the change in stress in the material caused by the acoustic wave as explained in more detail below. Although both transmit and receive amplitude regulators 11 and 15 may be used to advantage if the measurement system is based on a phase locked loop, as in the non-limiting examples described here, both are not necessary. Other measurement instruments may only vary the acoustic amplitude or power using other techniques.

The ultrasonic phase measurement instrument 10 phase locks to the signal corresponding to the reflected acoustic wave from the sample received via the receive amplitude regulator 15 and the amplifier 16. The phase measurement instrument 10 can, if needed or desired, measure very small changes in the propagation time of the acoustic wave in the sample 4. If, for example, the differential measurement instrument 10 generates a 2.25 MHz ultrasonic pulse, the instrument's resolution is 0.1 Hz or about parts per 10 million. Any change in the propagation of the acoustic pulse that alters the velocity (or propagation length) of that pulse by parts per 10 million can be measured. Stress is one example of a material characteristic that can alter the velocity or propagation length of the acoustic pulse as it propagates through the sample. Placing the sample under tension, for example, elongates the sample, and the velocity of the acoustic pulse either decreases or increases depending on the nonlinear properties of the material sample.

One non-limiting way to measure the velocity of the acoustic pulse moving through the material sample is to measure the time delay of the received acoustic pulse. The velocity of a wave is related to the time it takes for the wave to propagate the length of the material sample. Another approach is to phase-lock a single frequency tone-burst of waves in a sample and measure the change in frequency to achieve the next higher or lower lock point. The change in frequency of that phase-locked wave is inversely related to the propagation time. A characteristic of the material, such as stress or strain, affects the acoustic wave's velocity/frequency/phase. Changing the amplitude of the acoustic signal results in a change in the acoustic wave's velocity/frequency/phase. By determining that change or shift in the acoustic wave's velocity/frequency/phase, that characteristic of the material may be determined.

The ultrasonic measurement instrument 10 is a differential measurement device that measures the change or difference in velocity of the acoustic signal by measuring the change in the signal's phase. Differential measurements are very robust because they effectively cancel out offsets, biases, and other variables that affect the accuracy of absolute measurements. The velocity (V) of the acoustic wave measured by the differential measurement instrument 10 changes in accordance with the following relationship:

$$\Delta V/V = \eta(\Delta\epsilon/\epsilon) \quad (1)$$

where $\epsilon$ is the strain in the material sample and $\eta$ is a calibration constant relating strain $\epsilon$ to the normalized velocity $\Delta V/V$. For a material that is nonlinear, the change in the measured propagation parameter (e.g., the velocity or propagation length of the acoustic pulse) depends on the initial measurement point. This is illustrated in a simplified form in FIG. 6A which plots velocity V of the measured acoustic wave against strain $\epsilon$ in the material (strain is a change in length of the material).

FIG. 6A shows two curves: a linear curve and a nonlinear curve. A differential or change in the strain $\Delta\epsilon$ (i.e., a change in length of the material) produces a differential change in the velocity $\Delta V$ of the acoustic wave propagating through that material as shown in FIG. 6B. For a linear curve at strain (A), there is a 1-to-1 relationship between the frequency differentials and strain differentials (see 20). This is also the case at strain (B) (see 21) and at any strain along the linear curve. But for the nonlinear curve, a change in strain of one normalized unit at point B produces an acoustic velocity change of 0.8 (see 22), while a change in strain of one normalized unit at point C produces a much different acoustic velocity change in strain of 3 (see 23).

For the linear curve, all differential measurements produce a fixed outcome. If a material is nonlinear, that is not the case. Most materials are nonlinear. The well known Hook's law linking elongation times a stiffness constant, for example a spring constant, to applied force is only an approximation of how real materials behave. In fact, the real spring constant depends on elongation itself, which can be seen by expressing the stiffness as dependent on strain. That expression introduces higher-order elastic constants. Higher-order elastic constants are linked to engineering states/properties of applied stress, heat treatment, residual stress, and fatigue.

Using applied stress as an example, we explore the following stress-strain equation:

$$\sigma = k_2\epsilon + k_3\epsilon^2 + \ldots 2k(\epsilon)\epsilon \quad (2)$$

where $\sigma$ is the stress, $k_2$ is a second order "spring" constant, $k_3$ is a third order constant, and $\epsilon$ is the strain. The ultrasonic velocity $V^2$ is related to the elastic constant $k(\epsilon)$ and the material density $\rho$ by the following:

$$V^2 = k(\epsilon)/\rho \sim (k_2 - k_3\epsilon)\rho \quad (3)$$

Taking a strain derivative of this ultrasonic velocity equation (3) produces:

$$dV/d\epsilon = k_3/(2V\rho) \quad (4)$$

Thus, the strain derivative of the velocity of sound $V^2$ is a parameter directly linked to the third-order elastic or higher-order spring constants, a fundamental property of the material closely linked to nonlinear material behavior.

Based on these mathematical relationships, the stress of a material is determined by taking velocity derivatives to determine positional variations in the underlying stress state of the material nondestructively. The stress state of a material may be determined then by monitoring the change in the strain as a known change in external static stress is applied. For example, the differential strain of FIG. 6B can be a result of stress applied by a load frame. A load frame applies load directly to the sample by pulling or compressing the material. There are other ways to introduce loads or strains in a sample. Temperature and pressure will alter the state of a material and can be used for derivative purposes. Temperature, however, has a very slow time constant and thus requires a long measurement time period. Pressure requires an enclosure and can be dangerous. By keeping temperature and pressure constant, one can use an acoustic wave to produce strain.

Thus, differential strain is caused by altering the amplitude of the acoustic wave in the material. In other words, additional strain is introduced acoustically into the material by increasing the amplitude, energy, or power of the acoustic wave applied to the material. As a result, no other mechanical strain, stress, or other mechanical force needs to be applied to the material. Nor do the unloaded initial conditions of the material need to be measured or otherwise known in order to determine the material's stress.

For example, using the analog or digital phase locked loop measurement systems described earlier as a measurement device, a frequency (recall that the acoustic wave's velocity is related to its frequency) lock point may be established at quadrature for a given sample and for a given acoustic amplitude. The analog phase locked loop measurement system is suitable for measurement resolutions on the order of parts per ten million. The digital phase locked loop measurement system is suitable for measurement resolutions on the order of 100 parts per billion resolution. With sufficiently high resolution, very small changes in the velocity/time delay/frequency/phase of the acoustic wave propagation through the material that accompany differential strain or other characteristics of that material may be measured.

For the primary non-limiting example used in this description, the differential strain is produced by increasing the signal amplitude/power/energy on the transmit side so the acoustic strain in the material increases. At the same time, the system decreases the amplitude of the measured signal by the same amount provided back to the differential measurement instrument, thus keeping the signal amplitude fixed on the instrument receiver side. This may be accomplished, for example, using the transmit and receive amplitude regulators 11 and 15 shown in FIG. 5. The differential measurement can be made either by increasing or decreasing the amplitude/power/energy of the transmitted and/or received acoustic signal. The main point is to create a differential. As shown in FIG. 6A, if the curve of velocity vs. strain is nonlinear, the slope of that change corresponding to a strain derivative, i.e., the change in velocity over the change in strain, depends on the position along the strain axis. A strain derivative at strain point A is different from one acquired at strain points B or C. Therefore, the residual internal state of stress of a material may be determined by taking a strain derivative using the change in amplitude of the measurement of the acoustic wave in the sample.

Figure 7:
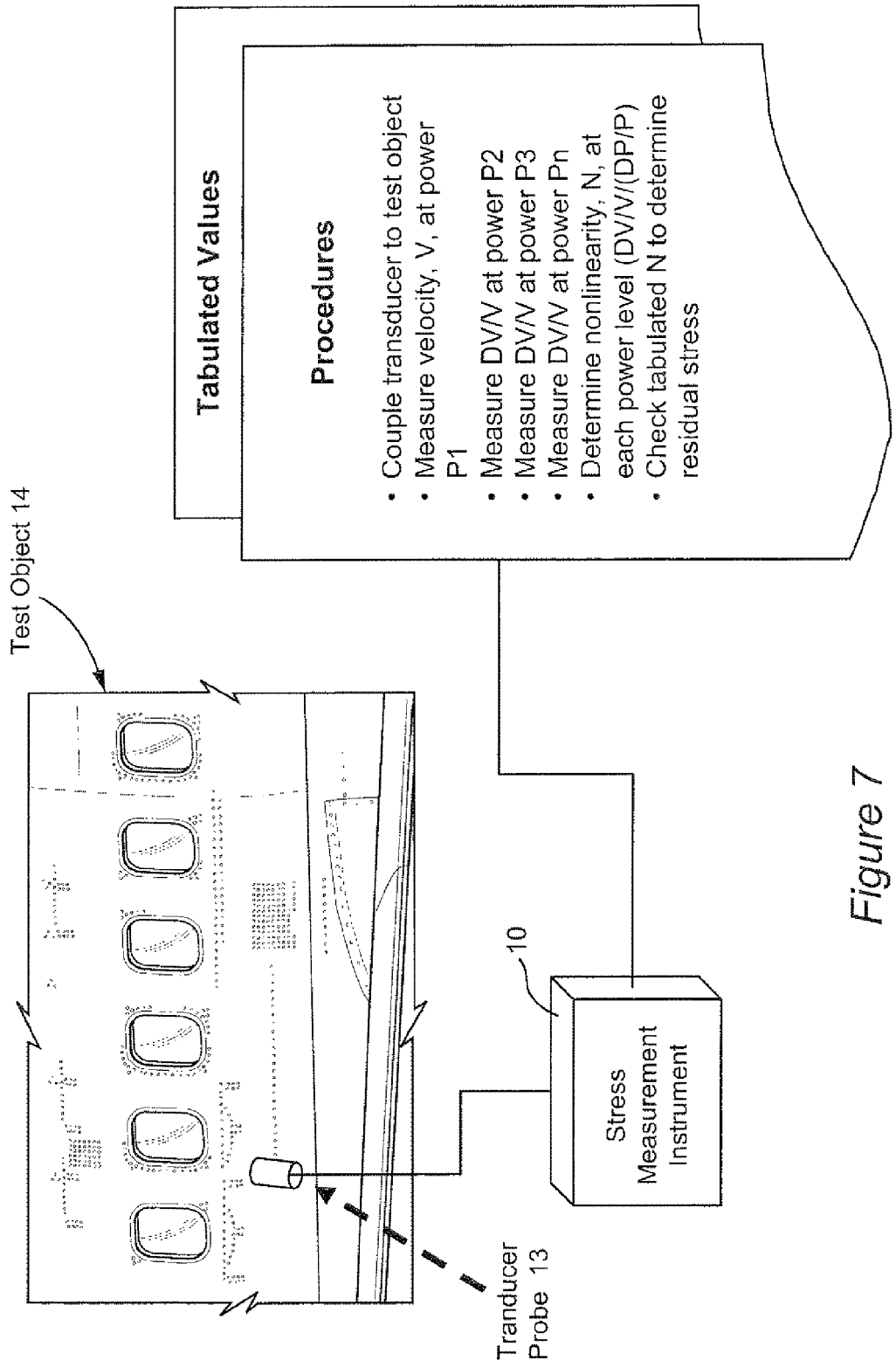
FIG. 7 shows an example of applying the material characteristic measurement system to measuring a residual stress of rivet holes in an airplane fuselage.

FIG. 7 shows a practical example application where the material characteristic measurement system may be used to measure a residual stress of rivet holes in an airplane fuselage 14. Commercial airplanes have hundreds of thousands rivet holes, all of which experience various degrees of stress and deformation during the airplanes useful life. This technology is very well suited to measure the residual stress of the material surrounding each of these holes quickly and accurately. The transducer is embodied in a portable movable probe 13 that is positioned either manually or automatically near each rivet hole. The probe 13 is connected to the stress measurement instrument 10, which for each hole, measures the velocity V of the reflected acoustic wave at a first power level. The stress measurement instrument 10 then measures the change in velocity DV of the reflected acoustic wave at a second different power level P2, third different power level P3, through n powers. A nonlinear slope parameter $N=(DV/V)/(DP/P)$ (the ratio of the normalized change in acoustic velocity to the normalized change in power of the acoustic wave) is determined at each power level and stored in a table. $DV=V_n - V_{n-1}$ and $DP=P_n - P_{n-1}$. $V_1$ and $P_1$ can be any practical value such as any where along the non-linear curve like that shown in FIG. 6A for the material being tested. N and n are not necessarily the same. Because the stress/strain relationship is non-linear, measurements may be taken at several different power levels, which enhance the accuracy of the determination of stress by reducing error through multiple measurements. The tabulated nonlinear slope parameters N for each hole are then checked to determine residual stress. This may be accomplished for an aircraft skin by performing a series of measurements along a rivet line of holes to map out the variations in residual stresses as a function of position along the fuselage. The technology described above detects as defective a hole that was not properly cold-worked to expand its diameter to produce residual compressive stresses.

In a preferred but still an example implementation, the tabulated values for a particular material are stored in a lookup table in memory in the stress measurement system over the practical range of values for the non-linear curve for a given material and possibly a given material conditioning, e.g., alloy and heat treatment. In this way, either the determined nonlinear parameter N can be used as an index to the lookup table to retrieve the corresponding stress for the material. Alternatively, the table could be configured so that DV/V is an index on one axis of the table and DP/P is another index on the other axis of the table. Yet another alternative is to store different values of the nonlinear parameter N in the table which can be accessed with a corresponding stress, and then the retrieved nonlinear parameter N may be converted into a stress or other material characteristic.

This approach may be more practical than other methods of assessing the stress or microstructure of a material. For example, if x-ray analysis were used, one would have to clear the area, bring in a radiation-producing device, and measure the backscattering angle separation of spots to determine the inter-atomic spacing from which one would calculate strains. The measurement only determines the stress where the x-ray beam strikes the material, so it is difficult to perform measurements over large areas. Also, the measurement is near the surface and not in the bulk of the material.

Figure 8:
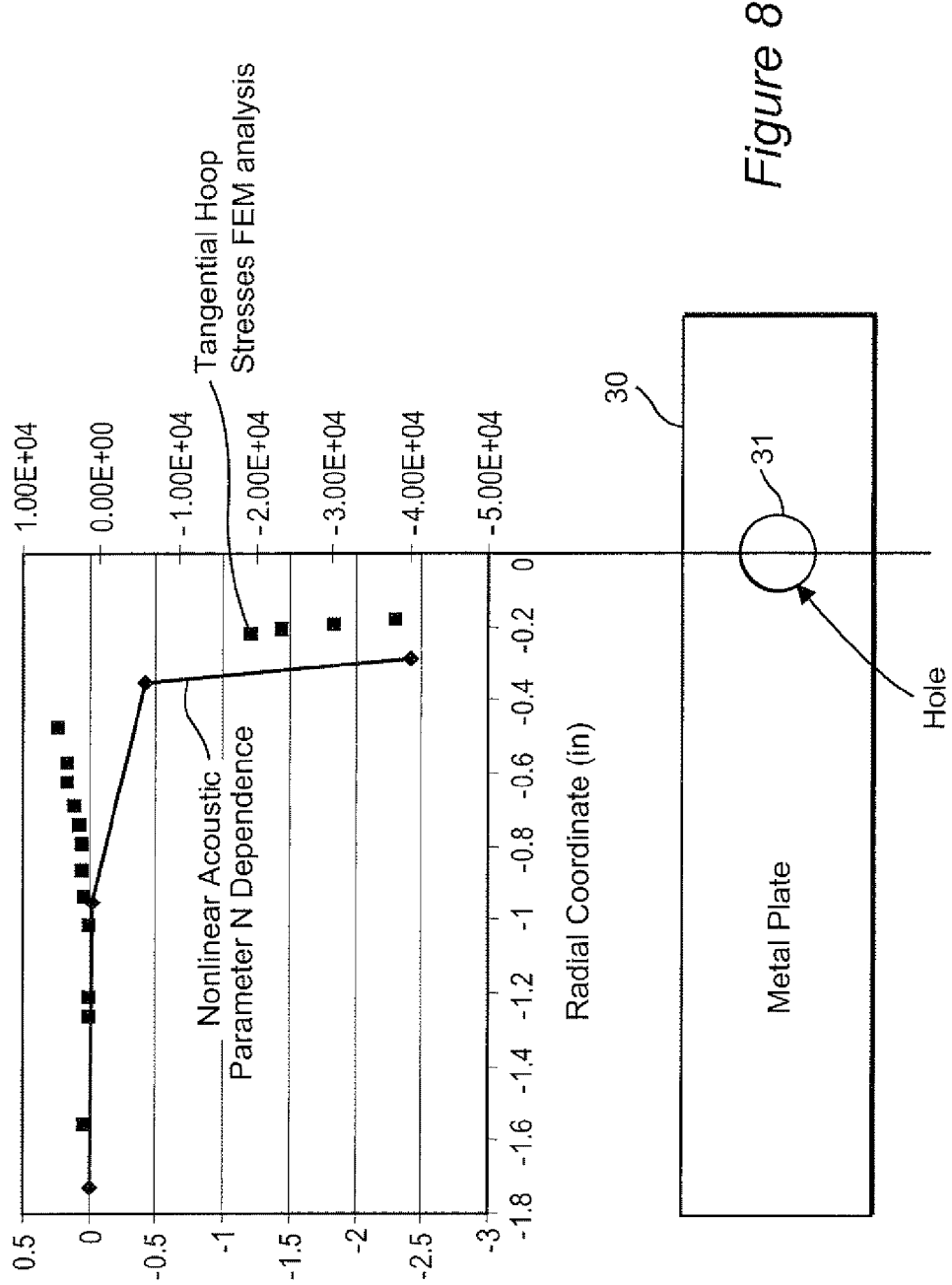
FIG. 8 is a graph illustrating example nonlinear measurements of stress in a metal plate with a hole.

FIG. 8 is a graph illustrating example nonlinear measurements of stress in a metal plate 30 with a hole 31, and in a particular, shows residual stress around a hole in a plate using a system based on that shown in FIG. 5 employing a digital phase locked loop differential measurement device like that referred to earlier. The hole 30 was subjected to plastic expansion to "build-in" residual compressive stress to extend the life of the hole in a fatigue environment. This is common practice in aerospace vehicles to increase the service life of the vehicle in a fatigue environment. The data was acquired by measuring the slope of the change in quadrature lock frequency or phase (recall that acoustic velocity is related to acoustic frequency, phase, and time delay) as a function of sampled acoustic amplitude. That slope is the nonlinear parameter N. The figure plots the nonlinear acoustic parameter N dependence as a unction of distance from a hole. Close to the hole, the nonlinear acoustic parameter varies dramatically as a function of distance from the hole. After about one inch from the hole it does not because the residual stress of the plate is relatively constant. The graph also shows a finite element analysis (FEM) calculated tangential hoop stress as a function of distance from the hole 31 in the metal plate 30. These FEM stress points are previously computed values of the stress obtained from a well-established model for this material being tested. In a typical FEM calculation, a solid is divided into many (e.g., millions) of small boxes with forces applied to each box. Strains for each box are calculated and summed to determine an over-all structure deformation. The ultrasonic curve agrees well with the FEM calculated stress points taking the size of the transducer (in this non-limiting example it was 0.5" across) into account as an averaging area.

Figure 9:
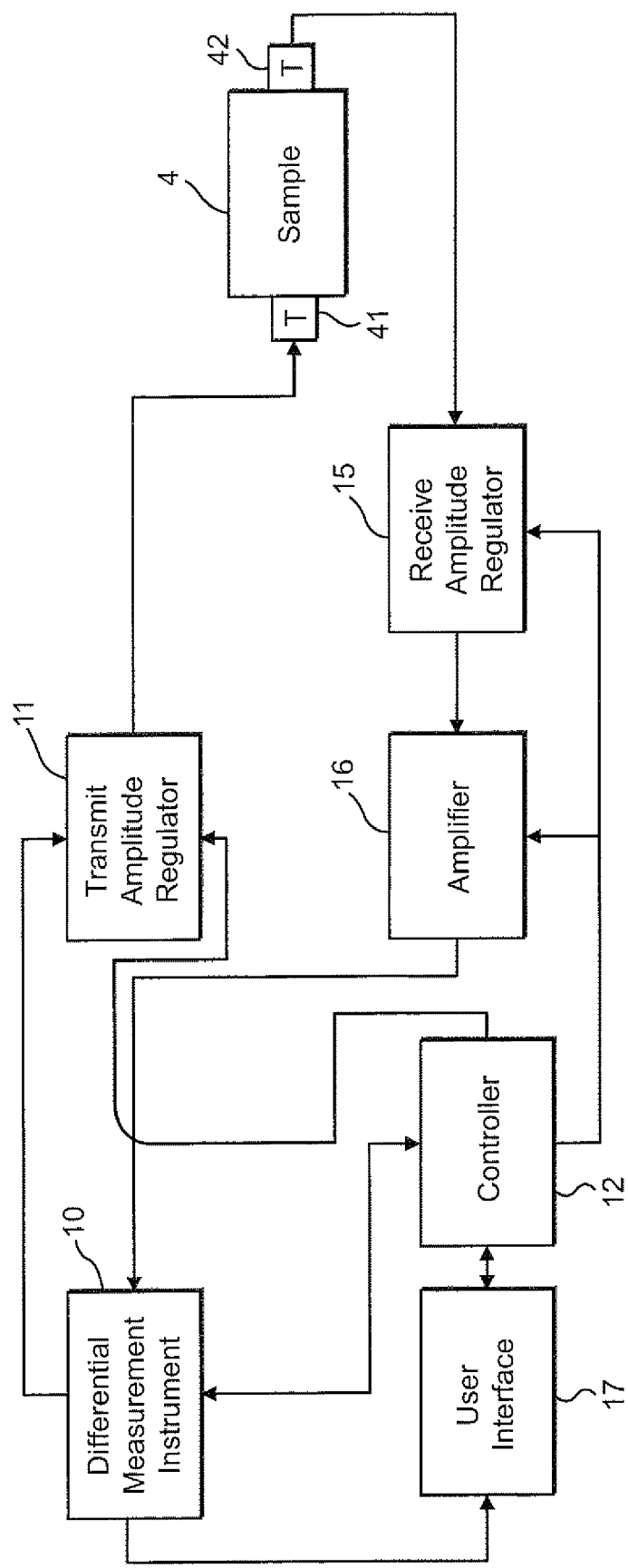
FIG. 9 is a function block diagram showing another non-limiting example of a material characteristic measurement device using a transmit and a receive transducer.

FIG. 9 is a function block diagram showing another non-limiting example of a material characteristic measurement device using a transmit transducer 41 provided on one side of the material sample 4 and a receive transducer 42 provided on the opposite side of the material sample 4. The transmitted ultrasonic pulse from the transmit transducer 41 propagates once through the material, rather than being reflected from the opposite side and the reflected wave detected, and the receive transducer 42 detects it, converts the acoustic wave into an electrical signal, and provides that signal to the receiver amplitude regulator 15. More than two transducers could be used. The same measurement is taken in terms of an amplitude derivative with the transmit amplitude regulator 11 being controlled by the controller 12 to alter the transmitted transducer 41 amplitude inversely with the receiver amplitude regulator 15 at the receiver transducer 42. As explained earlier, this keeps the received signal constant at the phase locked loop based measurement instrument while the acoustic amplitude in the material sample 4 increases and decreases to acquire the derivative slope parameter N.

In another non-limiting example embodiment, the locations of the receiver amplifier 16 and amplitude regulator 15 may be switched. This allows the systems to use present day variable gain amplifiers in a compact system where the signal has a preamplifier and then a variable gain amplifier followed by the fixed gain stage. Another non-limiting example embodiment replaces the transmit and receive amplitude regulators 11 and 15 with digitally-controlled amplifiers to change the acoustic intensity in the sample while keeping the signal strength processed in the instrument constant. This embodiment allows more rapid testing by a fully electronic control (e.g., no mechanical relays where the system needed to be disabled, relays switched, and then re-enabled).

It is not necessary that the change in velocity of the acoustic measurement wave be induced by a change in power of the acoustic measurement wave. For example, separate from the applied acoustic measurement wave, a first acoustic pumping wave may be applied to the material at a first power level followed by a second acoustic pumping wave applied to the material at a second, different power level. The change in power level in the material resulting from the first and second acoustic pumping waves causes a change in a velocity of the acoustic measurement wave propagating through the material. The change in velocity relative to the change in power level may then be used to determine the characteristic of the material.

Figure 10:
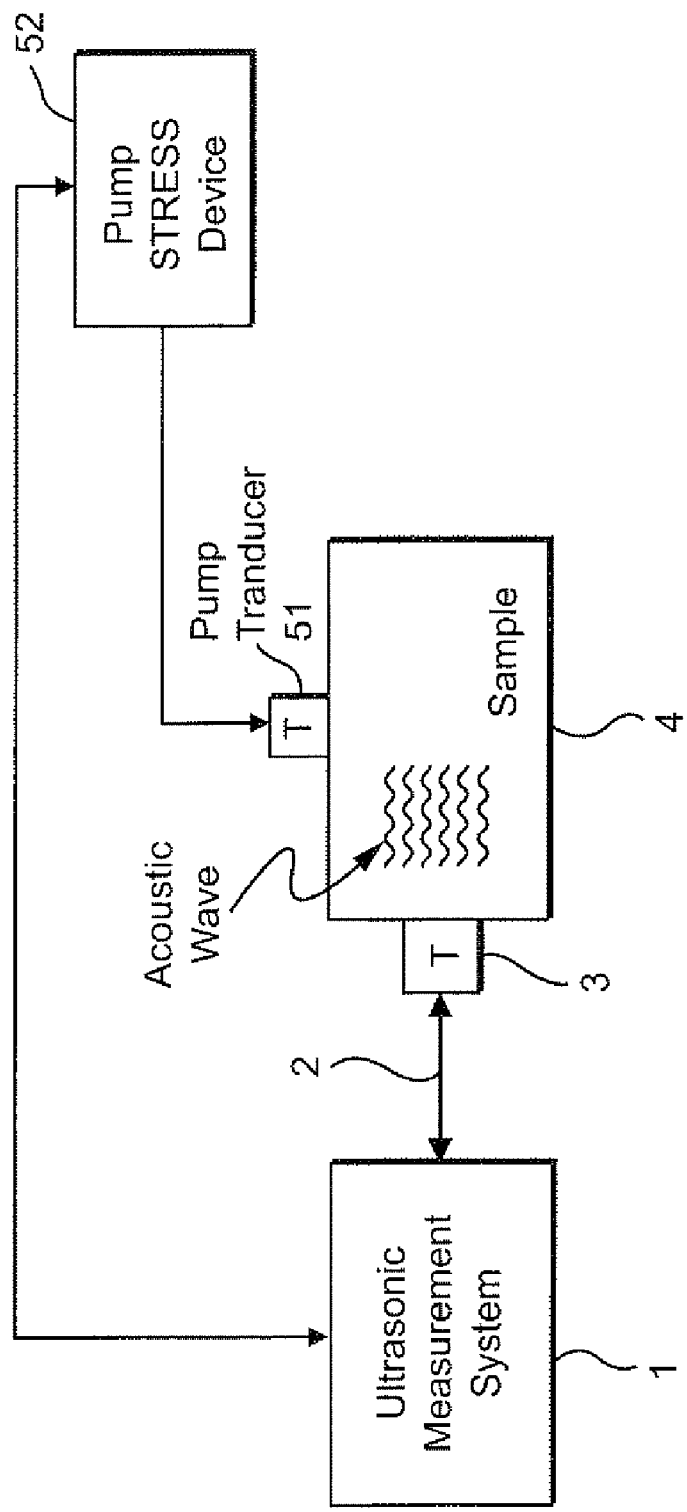
FIG. 10 is a function block diagram showing another non-limiting example of a material characteristic measurement device using a measurement transducer and pump transducer.

FIG. 10 is a function block diagram showing another non-limiting example of a material characteristic measurement device using a measurement transducer 3 and pump transducer 51. The pump transducer 51 is an independent source of acoustic energy to strain the material 4 while the stress measurement system detects the strain derivative using the reflected acoustic signal associated with the measurement transducer 3. A pump stress device 52 produces an adjustable amplitude electrical wave to drive the pump transducer. The pump signal is typically at a frequency different from the measurement wave frequency and only exists for a brief period of time when the measurement is taken. The pump stress device generates an acoustic field that is linked to the ultrasonic measurement system 1 so as to provide differential amplitudes required for the derivative measurement. The pump acoustic wave can be at any frequency and can be coupled to the material sample 4 at any location to alter the internal acoustic sample strain to be detected by the measurement transducer 3. If a phase locked loop-based measurement device is used, differential measurements can be achieved by synchronizing the measurement acoustic wave detected by transducer 3 to acquire a phase lock while the pump signal from pump transducer 51 is at maximum amplitude (compression) and then another measurement at minimum amplitude (rarefaction). The difference between these two measurements is caused by the nonlinear characteristic (e.g., residual stress) of the material sample. By sweeping the amplitude of the pump signal from zero to some number, the nonlinearity slope parameter N linked to stress, for this example, may be determined.

Figure 11:
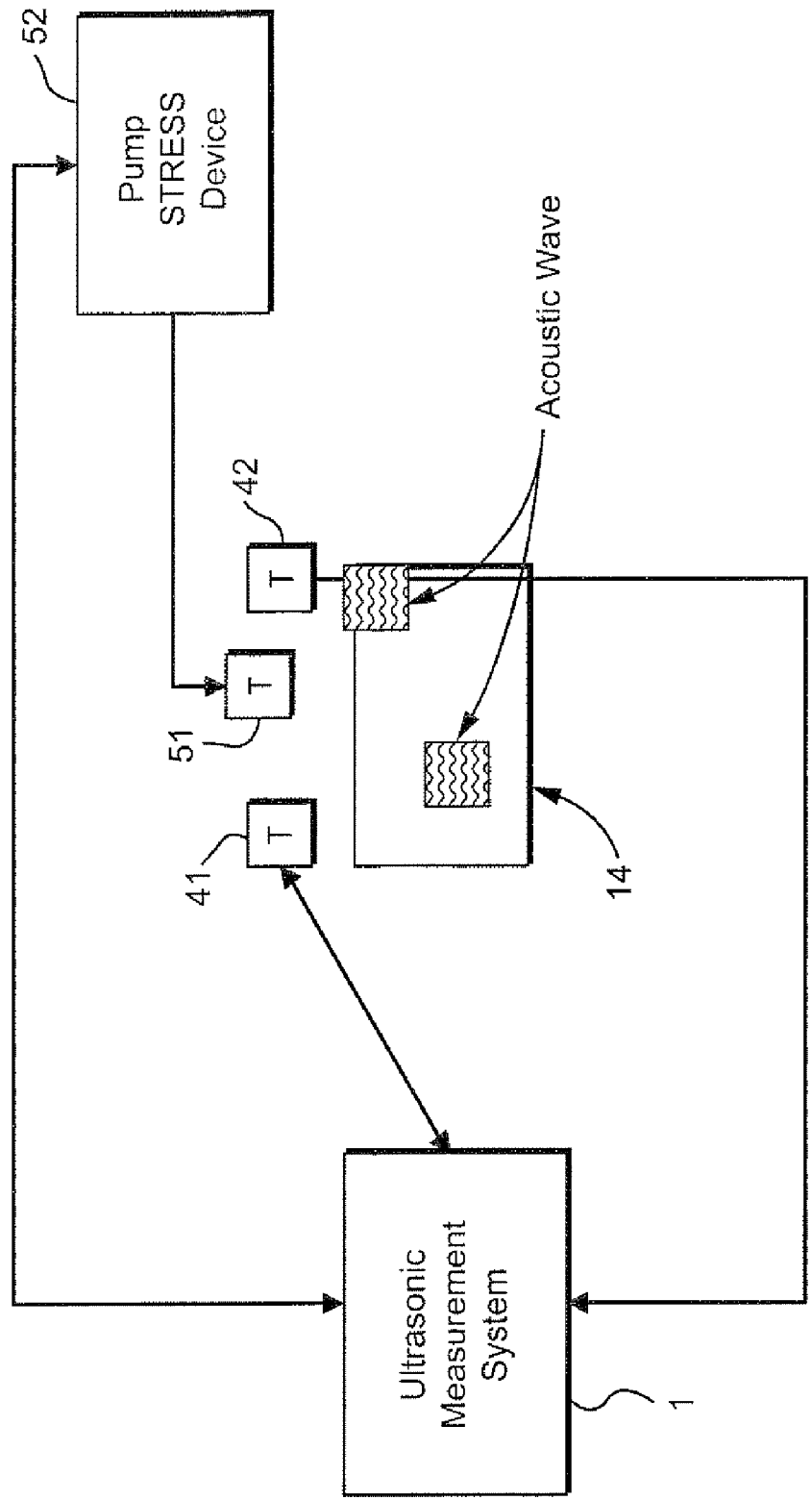
FIG. 11 is a function block diagram showing another non-limiting example of a material characteristic measurement device using transmit and receive measurement transducers and pump transducer.

FIG. 11 is a function block diagram showing another non-limiting example of a material characteristic measurement device using transmit and receive measurement transducers 41 and 42 and pump transducer 51. Some materials, such as sand, may be characterized for weight-bearing capability by taking the differential measurement as shown in this figure. Here, the material sample is saturated sand under water. The transmit transducer 41 launches an acoustic wave into water over the sand bottom. The acoustic wave propagates in the sand and is re-radiated back to the receiver transducer 42. The stress measurement system 1, which again in this example is a phase locked loop-based measurement device, locks to the received wave. The pump stress device 52 drives a changing acoustic wave into the sand performing the differential measurement to determine the effect of strain on the sand's behavior (e.g., soil strength). A parallel application substitutes plastics or composites for the sand. The measurements may also be made using single transducer and transmit and receive transducer approaches described above.

There are many applications of this technology. One example is to test the gas in a gas pipe through which natural gas is being pumped. By measuring the temperature and pressure of the gas by any suitable device(s) and the acoustic derivative with the differential measurement system 1, gas properties can be determined such as energy content, gas stiffness, and/or compressibility. In another example application, the material sample is a biological growth medium. As bio-activity (e.g., cell division and organism growth) occurs in the growth medium, the acoustic propagation in the medium changes. For example, as the number of cells increases, the elastic and density properties of the medium change. The differential measurement system 1 can determine the changes in the nonlinear properties of the biological growth medium by taking an amplitude derivative of the medium as described above. In this way, both second and third order elastic properties may be determined to assess the bio-activity.

As already described, the ultrasonic stress measurement system 1 has immediate and significant application to testing the residual stress in materials. For example, at this time, no practical, non-destructive testing approach can access the stress fields induced in holes in a structure to extend structural life. Other non-limiting example applications include aerospace materials, bridges, piping, wiring, welding, heat treatment, surface peening, plastics, and biological systems. In addition to stress, the system can determine other microstructure and nanostructure variations in a material caused for example by heat treatment, alloying, plastic deformation, cold-work, existence of strain fields from an interference-fit fastener in a material, mixture variation in nanostructures, bio-organizational order caused by growth in a culture medium, or chemical cross-linking in a polymer or other mixture or chemical linking mechanisms.

The ultrasonic stress measurement system 1 provides a nondestructive, low cost, rapid measurement of material properties such as stress and microstructural characterization that would require destructive measurements for conventional material diagnostics. It will greatly expand the capability of engineers to assess remaining life in a structure or material and to predict change or damage in a structure or material.

Although various example embodiments have been shown and described in detail, the claims are not limited to any particular embodiment or example. None of the above description should be read as implying that any particular element, step, range, or function is essential such that it must be included in the claims scope. Reference to an element in the singular is not intended to mean "one and only one" unless explicitly so stated, but rather "one or more." The scope of patented subject matter is defined only by the claims. The extent of legal protection is defined by the words recited in the allowed claims and their equivalents. All structural and functional equivalents to the elements of the above-described example embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. No claim is intended to invoke paragraph 6 of 35 USC §112 unless the words "means for" or "step for" are used. Furthermore, no feature, component, or step in the present disclosure is intended to be dedicated to the public regardless of whether the feature, component, or step is explicitly recited in the claims.

The invention claimed is:

1. A method for determining an inter-molecular property of a material, comprising:
   (a) acoustically adding an incremental amount of energy to the material;
   (b) determining a non-linear parameter of the material as a result of the acoustically added incremental energy, where the non-linear parameter is associated with a strain derivative for the material resulting from the acoustically added incremental energy; and
   (c) determining the inter-molecular property of the material using the determined non-linear parameter.

2. The method in claim 1, wherein an incremental amount of stress or strain is added to the material.

3. The method in claim 1, wherein the inter-molecular property of the material is one or more of the following: a residual stress existing in the material without any external mechanical force applied to the material, applied stress, a fatigue state associated with the material, the age of the material, an interference-fit fastener stress in a material, a bio-activity of a material, a nanostructure mixture of the material, a heat treatment of the material, a cross-linking of polymers in the material, a bio-growth organization of the material, a clotting factor of blood or blood-like material, a cure of an adhesive or sealant material, or the microstructure of the material.

4. The method in claim 1, wherein the strain derivative for the material resulting from the added incremental strain is determined as follows:
   applying to the material a first acoustic signal having a first amplitude;
   determining a first velocity of or time delay associated with the first acoustic signal propagating through the material;
   applying to the material a second acoustic signal having a second amplitude different than the first amplitude;
   determining a second velocity of or time delay associated with the second acoustic signal propagating through the material; and
   determining a difference between the first and second velocities or time delays related to a difference between the first arid second amplitudes to generate the strain derivative associated with the material.

5. The method in claim 1, wherein the acoustically adding step (a) includes propagating an acoustic wave through the material at a predetermined amplitude.

6. The method in claim 1, further comprising:
   establishing a table mapping different strain derivatives for the material to corresponding stress or strain values for the material, and
   looking up in the table a stress or strain value for the material corresponding to the determined strain derivative for the material.

7. The method in 1, wherein a relationship between the different strain derivatives to the corresponding stress or strain values for the material is nonlinear.

8. The method in claim 1, further comprising:
   using a differential measurement instrument to perform steps (a)-(c),
   wherein a resolution of the differential measurement instrument depends on the type of material.

9. The method in claim 8, wherein the differential measurement instrument uses a phase sensitive comparison method to detect the strain derivative.

10. The method in claim 1, further comprising:
    applying to the material an acoustic measurement wave;
    applying to the material a first acoustic pumping wave at a first power level;
    applying to the material a second acoustic pumping wave at a second different power level,
    wherein a change in energy in the material resulting from the different acoustic pumping waves causes a change in a velocity of the acoustic measurement wave propagating through the material, and
determining the non-linear parameter of the material based on the change in velocity relative to the change in energy level.

11. The method in claim 1, further comprising:
making a first measurement associated with the material subjected to a first acoustic energy;
making a second measurement associated with the material subjected to a second acoustic energy different than the first acoustic energy; and
performing the determining step (b) using the first and second measurements.

12. Apparatus for determining an inter-molecular property of a material, comprising:
a transducer for applying an acoustic signal to the material, and
electronic circuitry, connected to the transducer, configured to perform the following tasks:
(a) acoustically add an incremental amount of energy to the material via the transducer;
(b) determine a non-linear parameter of the material as a result of the acoustically added incremental energy, where the non-linear parameter is associated with a strain derivative for the material resulting from the acoustically added incremental energy; and
(c) determine the inter-molecular property of the material using the determined non-linear parameter.

13. The apparatus in claim 12, wherein the inter-molecular property of the material includes one of the following: a residual stress existing in the material without any external mechanical force applied to the material, applied stress, a fatigue state associated with the material, the age of the material, an interference-fit fastener stress in a material, a bio-activity of a material, a nanostructure mixture of the material, a heat treatment of the material, a cross-linking of polymers in the material, a bio-growth organization of the material, a clotting factor of blood or blood-like material, a cure of an adhesive or sealant material, or the microstructure of the material.

14. The apparatus in claim 12, wherein the electronic circuitry is configured to determine the strain derivative for the material resulting from the added incremental strain as follows:
apply to the material a first acoustic signal having a first amplitude;
determine a first velocity of or time delay associated with the first acoustic signal propagating through the material;
apply to the material a second acoustic signal having a second amplitude different than the first amplitude;
determine a second velocity of or time delay associated with the second acoustic signal propagating through the material; and
determine a difference between the first and second velocities or time delays divided by a difference between the first and second amplitudes to generate the strain derivative associated with the material.

15. The apparatus in claim 12, wherein the electronic circuitry is configured to:
establish a table mapping different strain derivatives for the material to corresponding stress or strain values for the material, and
look up in the table a stress or strain value for the material corresponding to the determined strain derivative for the material.

16. The apparatus in claim 12, wherein the electronic circuitry is a differential parameter measurement instrument,
wherein the differential measurement instrument is configured to use a phase sensitive comparison method to detect the strain derivative.

17. The apparatus in claim 12, further comprising:
a receive transducer for receiving the acoustic signal having propagated through the material.

18. The apparatus in claim 12, further comprising:
a pump transducer for applying a first acoustic pumping wave to the material at a first power level and a second acoustic pumping wave to the material at a second different power level,
wherein a change in power level in the material resulting from the first and second acoustic pumping waves causes a change in a velocity of the acoustic measurement wave propagating through the material, and
wherein the electronic circuitry is configured to determine the non-linear parameter based on the change in velocity relative to the change in power level.

19. The apparatus in claim 12, wherein the electronic circuitry is further configured to:
make a first measurement associated with the material subjected to a first acoustic energy;
make a second measurement associated with the material subjected to a second acoustic energy different than the first acoustic energy; and
determine the inter-molecular property of the material using the first and second measurements.

* * * * *